United States Patent
Alqahtani (10) Patent No.: US 11,224,499 B1
(45) Date of Patent: Jan. 18, 2022

(54) ORTHODONTIC ABSORBING RETRACTOR

(71) Applicant: King Abdulaziz University, Jeddah (SA)

(72) Inventor: Hamad Saeed Alqahtani, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/410,636

(22) Filed: Aug. 24, 2021

(51) Int. Cl.
    *A61F 13/20*      (2006.01)
    *A61C 19/00*      (2006.01)
    *A61C 9/00*      (2006.01)
    *A61F 13/531*      (2006.01)
    *A61F 13/53*      (2006.01)

(52) U.S. Cl.
    CPC .......... *A61C 9/0033* (2013.01); *A61C 19/001* (2013.01); *A61F 13/2008* (2013.01); *A61F 13/531* (2013.01); *A61F 2013/5315* (2013.01); *A61F 2013/530029* (2013.01)

(58) Field of Classification Search
    CPC . A61C 19/001; A61C 9/0033; A61F 13/2008; A61F 13/2005; A61F 13/2011; A61F 13/2017; A61F 13/20–2042; A61F 13/2051–2071; A61F 13/531; A61F 2013/530029; A61F 2013/5315
    USPC ........................................................ 433/136
    See application file for complete search history.

(56) References Cited

U.S. PATENT DOCUMENTS

| | | | |
|---|---|---|---|
| 1,010,146 A | 11/1911 | Ivory | |
| 2,099,931 A * | 11/1937 | Fourness | A61F 13/2051 604/364 |
| 2,897,597 A | 8/1959 | Ivory | |
| 2,930,128 A | 3/1960 | Berens | |
| 3,618,609 A | 11/1971 | Danbury | |
| 3,992,781 A | 11/1976 | Sturdivant | |
| 4,233,025 A | 11/1980 | Larson et al. | |
| 4,361,151 A * | 11/1982 | Fitzgerald | A61F 13/2062 604/15 |
| 4,705,514 A | 11/1987 | Barnard | |
| 5,199,872 A * | 4/1993 | Leal | A61B 1/24 433/136 |
| 9,549,860 B2 | 1/2017 | Foos | |

(Continued)

FOREIGN PATENT DOCUMENTS

| | | |
|---|---|---|
| DE | 1 022 353 B | 1/1958 |
| DE | 28 46 593 A1 | 9/1979 |

(Continued)

*Primary Examiner* — Susan S Su (74) *Attorney, Agent, or Firm* — Oblon, McClelland, Maier & Neustadt, L.L.P.

(57) ABSTRACT

An orthodontic absorbing retractor and methods for retracting regions of a mouth of a patient with the orthodontic absorbing retractor. The orthodontic absorbing retractor includes a braided cotton roll having a cylindrical shape, and has a central axis, a first end and a second end. The orthodontic absorbing retractor further includes a shape retention wire coaxially located within the braided cotton roll between the first end and the second end. The orthodontic absorbing retractor further includes a flexible hydrophobic plastic thread wrapped around an exterior of the braided cotton roll from the first end to the second end. The flexible hydrophobic plastic thread prevents sticking of the orthodontic absorbing retractor to an interior surface of the mouth.

13 Claims, 9 Drawing Sheets

(56) References Cited

U.S. PATENT DOCUMENTS

| | | |
|---|---|---|
| 2011/0229849 A1 | 9/2011 | Maurer et al. |
| 2015/0335495 A1* | 11/2015 | Wigder ............... A61F 13/2011 604/363 |
| 2018/0161534 A1* | 6/2018 | Allen, Jr. ............ B29C 48/0022 |
| 2018/0207036 A1* | 7/2018 | Chien ................... A61F 13/266 |

FOREIGN PATENT DOCUMENTS

| | | | |
|---|---|---|---|
| ES | 2523065 A1 * | 11/2014 | |
| FR | 2 403 782 A1 | 4/1979 | |
| KR | 10-2009141 B1 | 8/2019 | |
| WO | WO 2011/037589 A1 | 3/2011 | |
| WO | WO-2020180571 A * | 9/2020 | ......... A61F 13/2031 |

\* cited by examiner

ORTHODONTIC ABSORBING RETRACTOR

BACKGROUND

Technical Field

The present disclosure is directed to a dental appliance, and particularly, to an orthodontic absorbing retractor and methods for retracting regions of the mouth of patients with the orthodontic absorbing retractor.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Orthodontic procedures are performed to diagnose, prevent and correct abnormal alignment of teeth and jaws. The procedure is also performed to modify facial growth in case of any abnormality in skeletal jaws in growing individuals, which is known as dentofacial orthopedics. The procedure involves use of orthodontic braces and other appliances such as orthodontic tubes to correct abnormalities in the teeth and jaws. The orthodontic braces and tubes are made of stainless steel, plastic or porcelain. They are generally bonded to facial or lingual surface of the teeth. Orthodontic bonding is a sensitive procedure as moisture coming from saliva, gum fluids, blood and water should be carefully controlled. Moisture contamination of teeth surfaces can lead to weakening or failure of the bond between the braces and the teeth. Thus, keeping teeth dry and controlling saliva and other oral fluids are crucial for effective bonding procedure.

Various techniques are known to control the moisture during the bonding procedure. Such techniques include cheek retractors, lip expanders, cotton rolls and saliva ejectors. Cheek retractors are widely used, can make bonding of posterior region of the mouth difficult as the cheek retractors are not easy to move around on within the mouth, and cannot stretch to allow clear and direct vision of posterior teeth. Dry field isolation is challenging, especially with regard to second molar teeth, when the orthodontic tubes are used in the bonding procedure. Dry field isolation is performed on one side at a time to control moisture contamination from saliva, thus retracting buccal mucosa can be unpleasant to the patient. Use of cotton rolls and a dental mirror for retraction and isolation may be a hectic procedure as the cotton rolls may get displaced any time, which may increase moisture contamination risk. Cotton rolls placed in lingual or facial vestibules can come out easily and suddenly, which can obstruct working area of the mouth during the bonding procedure. Further, the cotton rolls can not exert any active pressure on lips or cheek to improve visibility during the bonding procedure.

US20110229849A1 relates to a dental retraction device made from a yarn having twisted alginate fibers and an outer wire wrapped around the yarn. The wire may be a metal wire or plastic. However, this dental retraction device lacks the shape retention wire of the present disclosure, so cannot provide a retraction force against the gums or soft tissue of the mouth.

U.S. Pat. No. 9,549,860B2 relates to a dental isolator having an absorbent member made from a cotton roll and a retainment member made from a dental nylon in the form of a dental floss. The retainment member allows the dental isolater to form a U-shape, however, the isolater lacks features to form any other shape to conform with a shape of the teeth structure of the patient. Further, the dental isolater lacks features to provide stability when bent into the U-shape and does not have any features to avoid sticking of the isolator with interior of the mouth.

Each of the aforementioned patent references suffers from one or more drawbacks hindering their adoption. Accordingly, it is one object of the present disclosure to provide an orthodontic absorbing retractor and methods for retracting regions of a mouth of a patient with the orthodontic absorbing retractor, which provides effective isolation and retraction of the regions of the mouth during an orthodontic procedure.

SUMMARY

In an exemplary embodiment, an orthodontic absorbing retractor for use in a mouth of a patient is described. The orthodontic absorbing retractor includes a braided cotton roll having a cylindrical shape. The braided cotton roll has a central axis, a first end and a second end. The orthodontic absorbing retractor further includes a shape retention wire coaxially located within the braided cotton roll between the first end and the second end. The orthodontic absorbing retractor further includes a flexible hydrophobic plastic thread wrapped around an exterior of the braided cotton roll from the first end to the second end. The flexible hydrophobic plastic thread is configured to prevent sticking of the orthodontic absorbing retractor to an interior surface of the mouth.

In another exemplary embodiment, a method for retracting regions of a working area of a mouth with an orthodontic absorbing retractor is described. The method includes compressing the regions away from the working area by bending a shape retention wire located within the orthodontic absorbing retractor to follow a contour of the regions and inserting the orthodontic absorbing retractor into the mouth. The method further includes wicking moisture in the mouth by a braided cotton roll located on the orthodontic absorbing retractor and removing the orthodontic absorbing retractor without sticking to the regions in which sticking to the regions is prevented by a flexible hydrophobic plastic thread surrounding the braided cotton roll.

In another exemplary embodiment, a method for retracting regions of a mouth with an orthodontic absorbing retractor is described. The method includes bending a shape retention wire located within the orthodontic absorbing retractor into a C-shaped bend before inserting the orthodontic absorbing retractor into the mouth. The method further includes inserting the orthodontic absorbing retractor such that the C-shaped bend is proximate a parotid papilla gland in a buccal vestibule region of the mouth. A first end of the orthodontic absorbing retractor presses against an upper gum region of the mouth and a second end of the orthodontic absorbing retractor presses towards a lower gum region of the mouth. The method further includes pressing the orthodontic absorbing retractor against a side of the mouth to isolate the upper gum region and the lower gum region from a cheek wall of the mouth. The method further includes wicking moisture in the mouth by a braided cotton roll surrounding the shape retention wire and removing the orthodontic absorbing retractor.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of this disclosure are directed to an orthodontic absorbing retractor for use in a mouth of a patient and methods for retracting regions of the mouth of the patient with the orthodontic absorbing retractor. The orthodontic absorbing retractor includes a braided cotton roll having a cylindrical shape, which is wrapped with a flexible hydrophobic plastic thread to maintain integrity thereof and to prevent the orthodontic absorbing retractor from sticking to the gingiva and mucosa. A shape retention wire is provided in the middle of the braided cotton roll to allow the orthodontic absorbing retractor to maintain a shape when it is bent.

Figure 1:
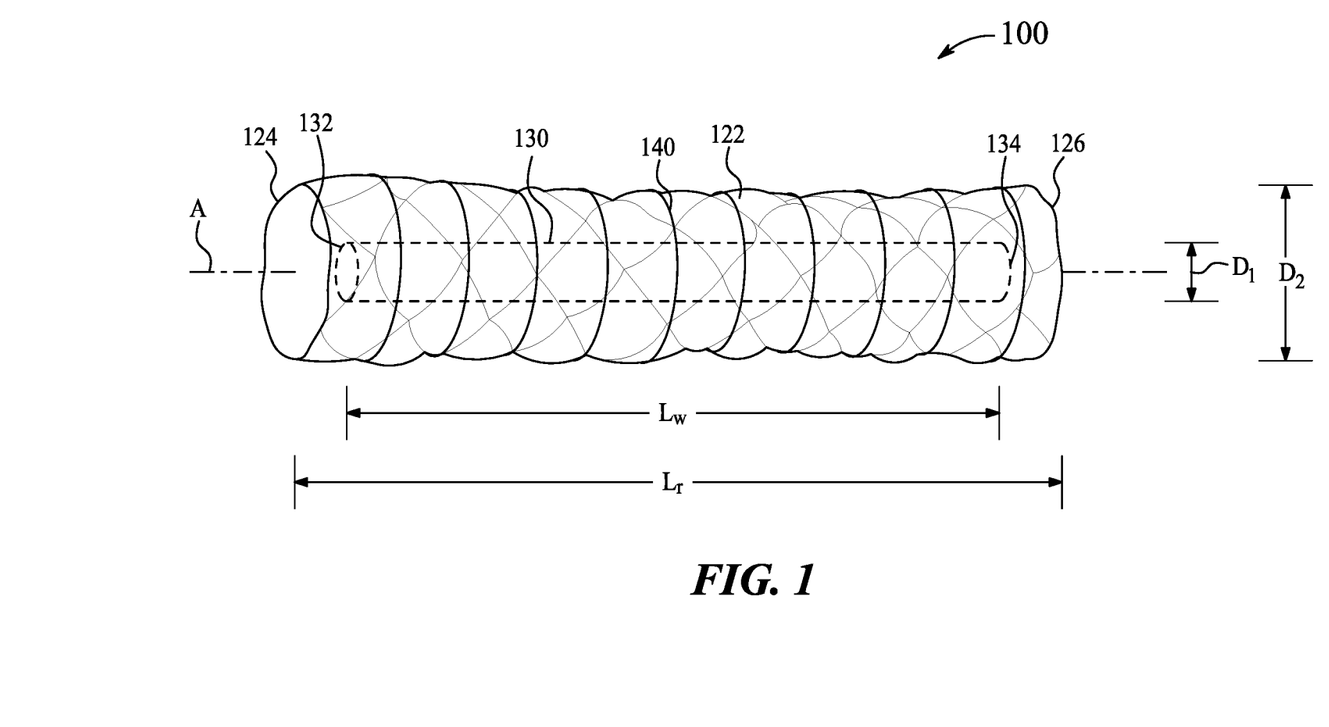
FIG. 1 is a perspective view of an orthodontic absorbing retractor, according to certain embodiments.

Referring to FIG. 1, a perspective view of an orthodontic absorbing retractor 100 is illustrated. The orthodontic absorbing retractor 100 is used for retracting regions of a mouth 102 of a patient during an orthodontic procedure. The orthodontic procedure is generally performed to diagnose, prevent, or correct abnormal alignment of teeth and thereby to avoid incorrect bite situations.

The abnormal teeth alignment may be in a lower teeth structure 104, otherwise known as the mandibular teeth, or an upper teeth structure 106, otherwise known as the maxillary teeth. During the orthodontic procedure, moisture coming from saliva, gum fluids, blood and water are absorbed by using the orthodontic absorbing retractor 100. The orthodontic absorbing retractor 100 is placed in a working area 108 of the mouth 102 of the patient to retract the regions thereof and to absorb the moisture from the working area 108. The orthodontic absorbing retractor 100 may be further defined as a device used to retract soft dental tissue, such as gingival tissue, away from hard tissue, such as teeth, during the orthodontic procedure.

The orthodontic absorbing retractor 100 includes a braided cotton roll 122 having a cylindrical shape. The braided cotton roll 122 includes cotton filaments. In one example, the braided cotton roll 122 may be formed from the cotton filaments as a single piece in the cylindrical shape and braided using a thread made of cotton. In another example, the braided cotton roll 122 may be formed from multiple strands of cotton filaments and braided together to define the cylindrical shape. The braided cotton roll 122 has a central axis 'A' and a roll length '$L_r$' defined between a first end 124 and a second end 126 thereof. The first end 124 and the second end 126 of the braided cotton roll 122 are alternatively referred to as the first end 124 and the second end 126, respectively, of the orthodontic absorbing retractor 100.

The orthodontic absorbing retractor 100 further includes a shape retention wire 130 coaxially located within the braided cotton roll 122 between the first end 124 and the second end 126 thereof. Particularly, the shape retention wire 130 is longitudinally disposed within the braided cotton roll 122 along the central axis 'A' thereof. The shape retention wire 130 has a wire length '$L_w$' defined between a first wire end 132 and a second wire end 134 thereof. The first wire end 132 of the shape retention wire 130 is placed near the first end 124 of the braided cotton roll 122 and the second wire end 134 of the shape retention wire 130 is placed near the second end 126 of the braided cotton roll 122. Each of the first wire end 132 and the second wire end 134 of the shape retention wire 130 may have a rounded end shape. During the orthodontic procedure, injuries to gum and interior of the mouth 102, which may be otherwise caused due to sharp edges, may be avoided due to the rounded shape of the first wire end 132 and the second wire end 134 of the shape retention wire 130. The wire length '$L_w$' of the shape retention wire 130 is less than the roll length '$L_r$' of the braided cotton roll 122, i.e., $L_w < L_r$. In a non-limiting example, the wire length '$L_w$' of the shape retention wire 130 is in a range of 3.0 to 5.6 inches long and the roll length '$L_r$' of the braided cotton roll 122 is in a range of 3.4 to 6.0 inches long. As such, the first wire end 132 and the second wire end 134 of the shape retention wire 130 are positioned inside of the first end 124 and the second end 126, respectively, of the braided cotton roll 122. Such arrangement of the shape retention wire 130 within the braided cotton roll 122 avoids direct contact of the shape retention wire 130 with the gum as the first end 124 and the second end 126 of the braided cotton roll 122 fully enclose the first wire end 132 and the second wire end 134 of the shape retention wire 130, respectively, and thereby avoid injuries to the gum during the orthodontic procedure.

The shape retention wire 130 is made of a biocompatible metal and has a circular cross-section having a first diameter '$D_1$'. In one example, the shape retention wire 130 is made of copper. In another example, the shape retention wire 130 is made of aluminum. The first diameter '$D_1$' of the shape retention wire 130 is less than a second diameter '$D_2$' defined by the cylindrical shape of the braided cotton roll 122, where $D_1<D_2$. In a non-limiting example, the first diameter '$D_1$' of the shape retention wire 130 is in a range of 0.025 inches to 0.035 inches and the second diameter '$D_2$' is in a range of 0.3 inches to 0.4 inches. Preferably, the first diameter '$D_1$' of the shape retention wire 130 is 0.03 inches and the second diameter '$D_2$' of the braided cotton roll 122 is 0.375 inches.

The orthodontic absorbing retractor 100 further includes a flexible hydrophobic plastic thread 140 wrapped around an exterior of the braided cotton roll 122 from the first end 124 to the second end 126. The flexible hydrophobic plastic thread 140 is configured to prevent sticking of the orthodontic absorbing retractor 100 to an interior surface of the mouth 102. The interior surface may be defined as a surface corresponding to the working area 108 of the mouth 102 of the patient. For example, the interior surface may correspond to interior skin surface of the cheek, gum, lips, and tongue. The flexible hydrophobic plastic thread 140 is made of a biocompatible hydrophobic material such that the orthodontic absorbing retractor 100 is not toxic. In one non-limiting example, the biocompatible hydrophobic material is a medical grade nylon. In another non-limiting example, the biocompatible hydrophobic material is polytetrafluoroethylene.

Figure 2A:
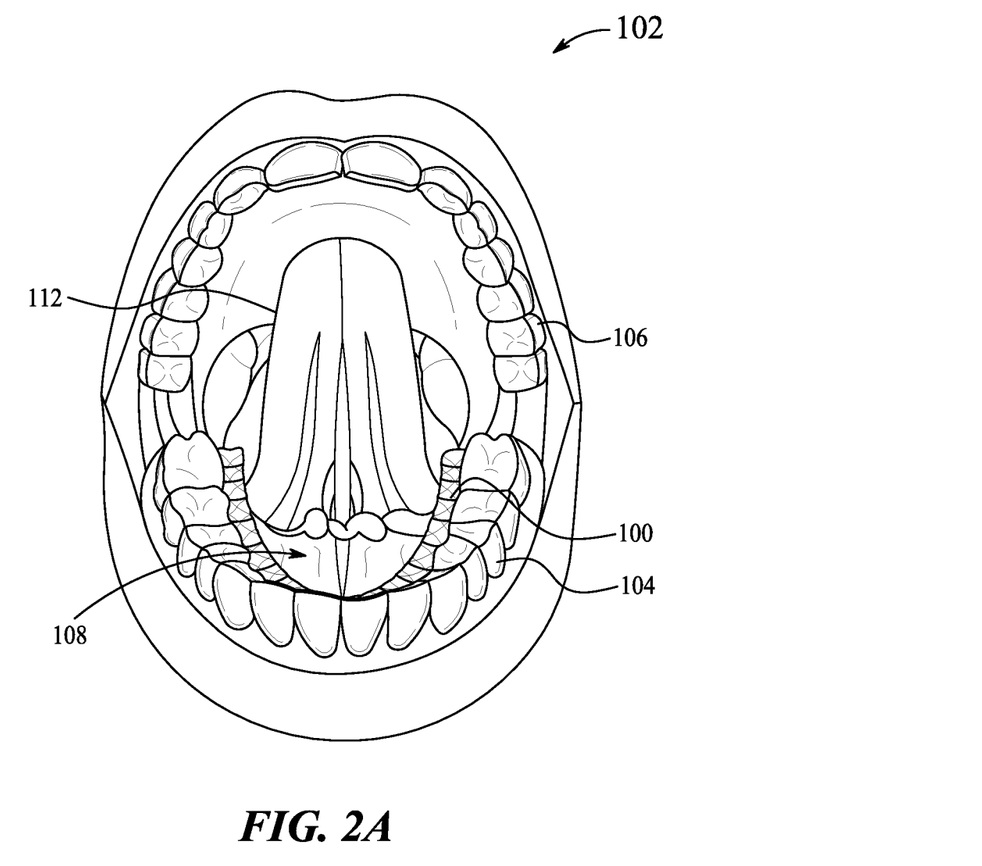
FIG. 2A is a schematic perspective view of a mouth of a patient showing the orthodontic absorbing retractor placed beneath a lower teeth structure, according to certain embodiments.

Referring to FIG. 2A, a schematic perspective view of the mouth 102 of the patient having the orthodontic absorbing retractor 100 placed therein is illustrated. Referring to FIG. 1 and FIG. 2A, the orthodontic absorbing retractor 100 is placed in the working area 108, such as the lower front teeth region of the mouth 102 of the patient, where the orthodontic procedure may be performed to fix abnormalities in the lower teeth structure 104. Particularly, the orthodontic absorbing retractor 100 may be placed beneath the lower front teeth region and a tongue region of the mouth 102. The lower front teeth region may be a surface or a portion of the lower teeth structure 104 defined by a facial surface, a lingual surface, an occlusal surface, or a combination thereof. The tongue region may be a surface or a portion defined by floor of the mouth 102 and an underside of tongue 112. The orthodontic absorbing retractor 100 is formed as a U-shaped bend and placed beneath the lower front teeth region and the tongue region of the mouth 102. The U-shaped bend of the orthodontic absorbing retractor 100 may conform to a U-shape shape of the lower teeth structure 104 such that the orthodontic absorbing retractor 100 may align with a contour of a gum region beneath the lower front teeth region of the mouth 102. Due to the spring strength of the shape retention wire, the orthodontic absorbing retractor 100 presses firmly against the contour of the gum region beneath the lower front teeth region of the mouth 102 to retract and isolate the region. The gum region may be defined as an interior surface of a gum corresponding to the lower teeth structure 104. When the orthodontic absorbing retractor 100 is placed beneath the lower front teeth region, the U-shaped bend faces towards a front region of the mouth 102 and the first end 124 and the second end 126 of the orthodontic absorbing retractor 100 face towards a back region of the mouth 102. The front region of the mouth 102 may be a region defined by canine and incisor teeth of the lower teeth structure 104 and the back region of the mouth 102 may be a region defined by molar and premolar teeth of the lower teeth structure 104. The first end 124 and the second end 126 of the orthodontic absorbing retractor 100 may be at a wider angle than a U-shape defined by posterior teeth of the lower teeth structure 104 in order to cause pressure on lingual side of the lower teeth structure 104 for stabilization. The first end 124 and the second end 126 of the orthodontic absorbing retractor 100 are placed at left and right sides of the lingual surface of the lower teeth structure 104 at the same time, thus reducing orthodontic procedure time and providing a comfortable experience for the patient.

In one example, the working area 108 may be defined as an upper front teeth region of the mouth 102 where the orthodontic procedure may be performed to fix abnormalities in the upper teeth structure 106.

Figure 2B:
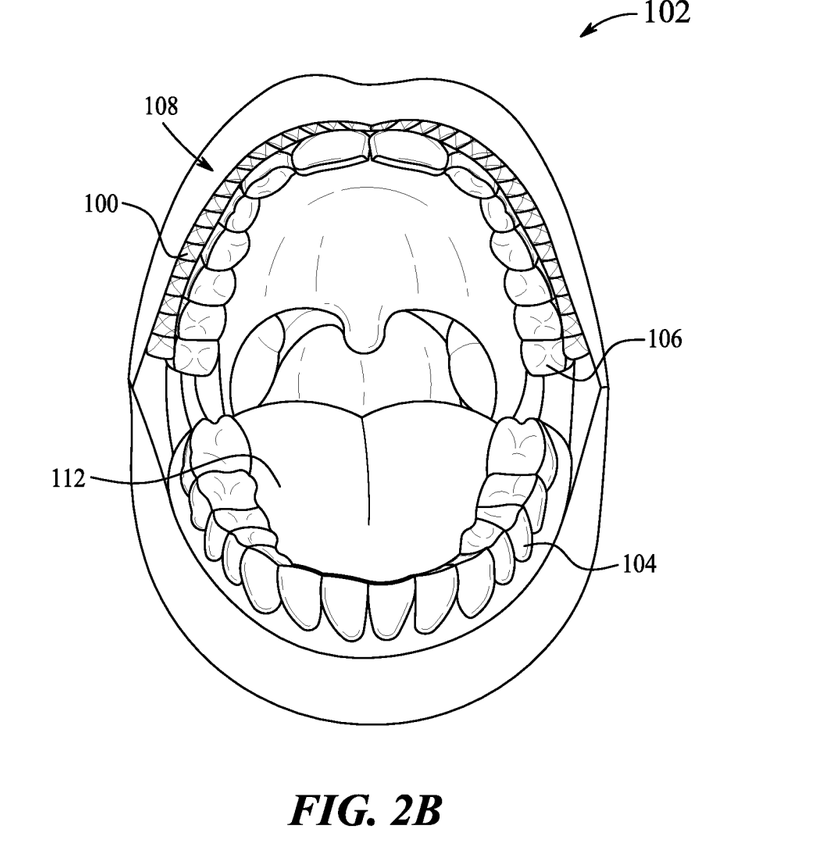
FIG. 2B is a schematic perspective view of the mouth of the patient showing the orthodontic absorbing retractor placed between an upper teeth structure and an upper lip, according to certain embodiments.

Referring to FIG. 2B, a schematic perspective view of the mouth 102 of the patient showing the orthodontic absorbing retractor 100 placed above the upper teeth structure 106 is illustrated. Particularly, the orthodontic absorbing retractor 100 is placed between the upper front teeth region and an upper lip region of the mouth 102. The upper front teeth region may be a surface or a portion of the upper teeth structure 106 defined by a facial surface, a lingual surface, an occlusal surface, and a combination thereof. The upper lip region may be an interior surface or a portion defined by the upper lip. The orthodontic absorbing retractor 100 is formed as a U-shaped bend and placed above the upper front teeth region and the upper lip region of the mouth 102. The U-shaped bend of the orthodontic absorbing retractor 100 may be adjusted to conform with a U-shape of the upper teeth structure 106 such that the U-shaped bend may align with a contour of a gum region above the upper front teeth region of the mouth 102. Further, the orthodontic absorbing retractor 100 presses against the contour of the gum region above the upper front teeth region of the mouth 102. The gum region may be defined as an exterior surface of a gum corresponding to the upper teeth structure 106. When the orthodontic absorbing retractor 100 is placed above the upper front teeth region, the U-shaped bend faces towards a front region of the mouth 102 and the first end 124 and the second end 126 of the orthodontic absorbing retractor 100 face towards a back region of the mouth 102. The front region of the mouth 102 may be a region defined by canine and incisor teeth of the upper teeth structure 106 and the back region of the mouth 102 may be a region defined by molar and premolar teeth of the upper teeth structure 106.

Figure 2C:
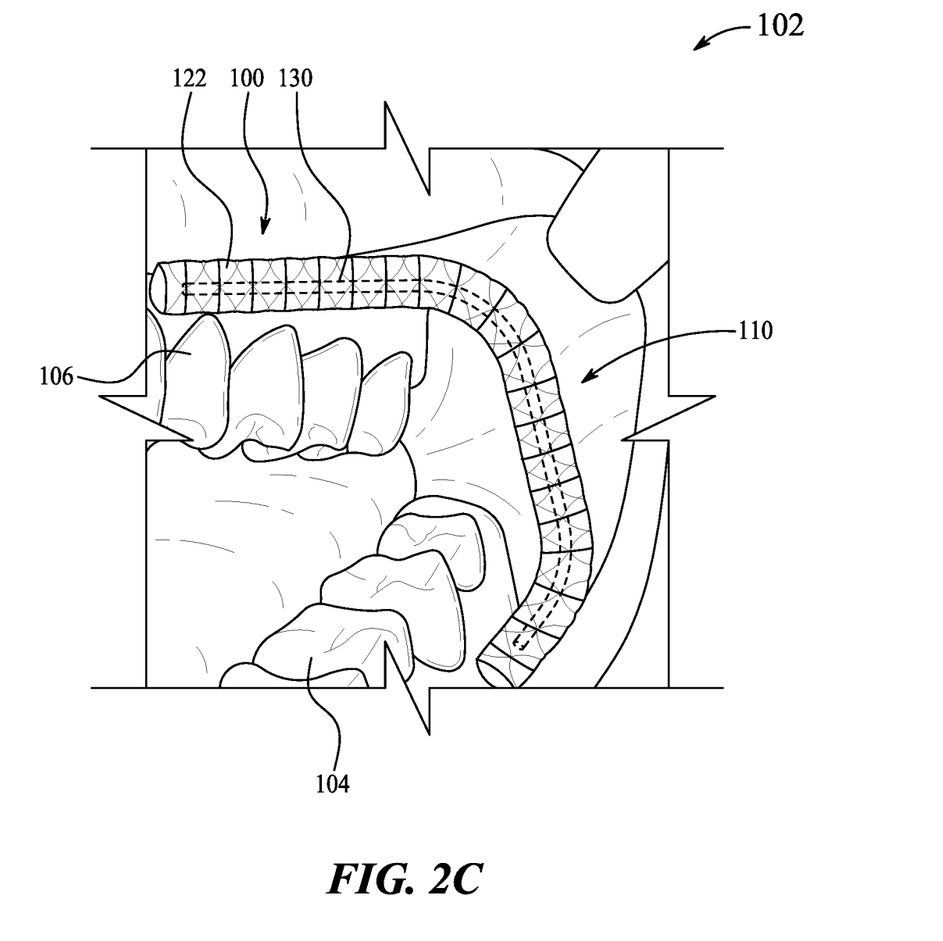
FIG. 2C is a schematic enlarged view of a portion of the mouth showing the orthodontic absorbing retractor bent into a C-shape and placed proximate a parotid papilla gland in a buccal vestibule region of the mouth, according to certain embodiments.

Referring to FIG. 2C, the working area 108 may be defined as a location proximate a parotid papilla gland in a buccal vestibule region 110 of the mouth 102. The buccal vestibule region 110 of the mouth 102 may be further defined as a location of the molar teeth, especially second molar teeth, of the upper teeth structure 106 and the lower teeth structure 104.

FIG. 2C illustrates a schematic enlarged view of a portion of the mouth 102 of the patient showing the orthodontic absorbing retractor 100 bent into a C-shape and placed proximate the parotid papilla gland in the buccal vestibule region 110 of the mouth 102 is illustrated. The orthodontic absorbing retractor 100 is formed as a C-shaped bend and placed proximate the buccal vestibule region 110 of the mouth 102. The shape retention wire 130 of the orthodontic absorbing retractor 100 is bent to form the C-shape. The C-shaped bend of the orthodontic absorbing retractor 100 may be adjusted to conform with a shape of the upper teeth structure 106 and the lower teeth structure 104 such that the C-shaped bend may align with a contour of an upper gum region and a lower gum region, respectively. The orthodontic absorbing retractor 100 presses against a side of the mouth 102 to isolate the upper gum region and the lower gum region from a cheek wall of the mouth 102. The upper gum region may be defined as an exterior surface of the gum corresponding to the upper teeth structure 106 and the lower gum region may be defined as an exterior surface of the gum corresponding to the lower teeth structure 104.

Figure 2D:
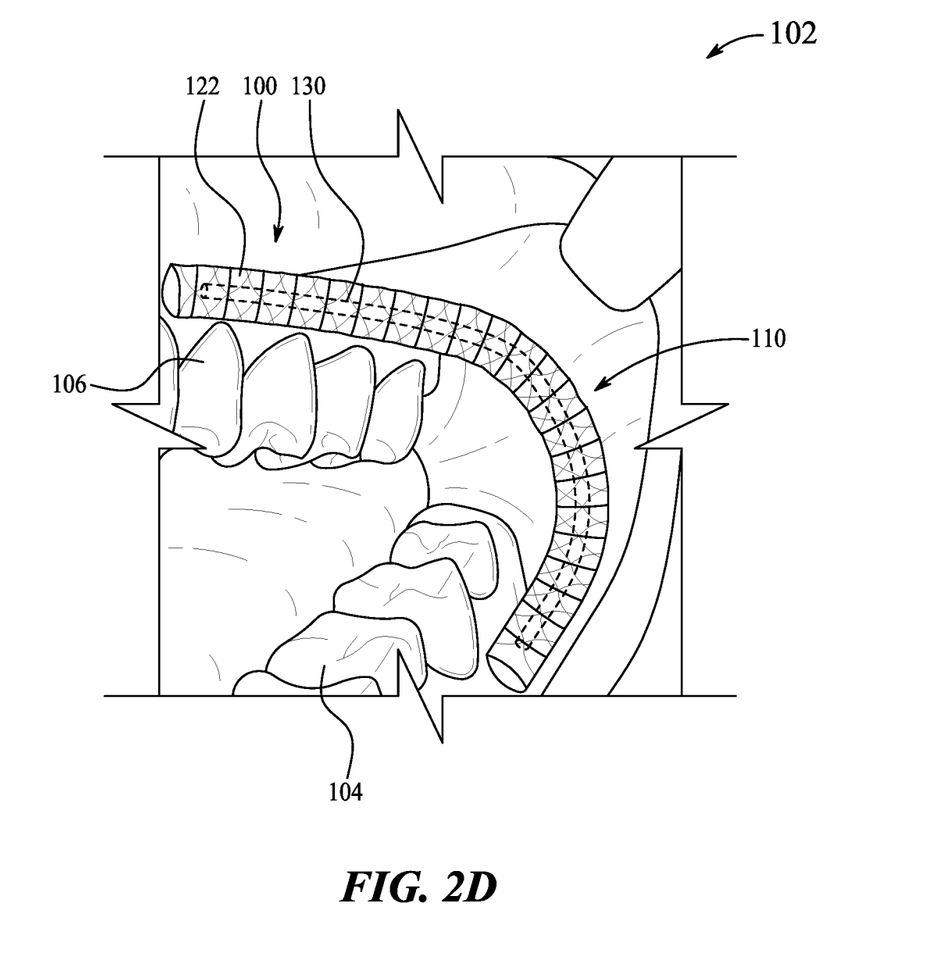
FIG. 2D is a schematic enlarged view of a portion of the mouth showing the orthodontic absorbing retractor bent into a U-shape and placed proximate the parotid papilla gland in the buccal vestibule region of the mouth, according to certain embodiments.

Referring to FIG. 2D, a schematic enlarged view of a portion of the mouth 102 of the patient showing the orthodontic absorbing retractor 100 bent into a U-shape and placed proximate the parotid papilla gland in the buccal vestibule region 110 of the mouth 102 is illustrated. The orthodontic absorbing retractor 100 can be bent into a U-shape and inserted into the mouth 102 of the patient such that the first end 124 and the second end 126 face towards the front region of the mouth 102. The first end 124 and the second end 126 of the orthodontic absorbing retractor 100 may be opened wider than a shape defined by second molar teeth of the lower teeth structure 104 and the upper teeth structure 106 to cause a pressure at the vestibules of the upper teeth structure 106 and the lower teeth structure 104 in the same working area 108, which is aided by asking the patient to close the mouth 102 slightly to allow more pressure and thus more retraction.

Figure 3A:
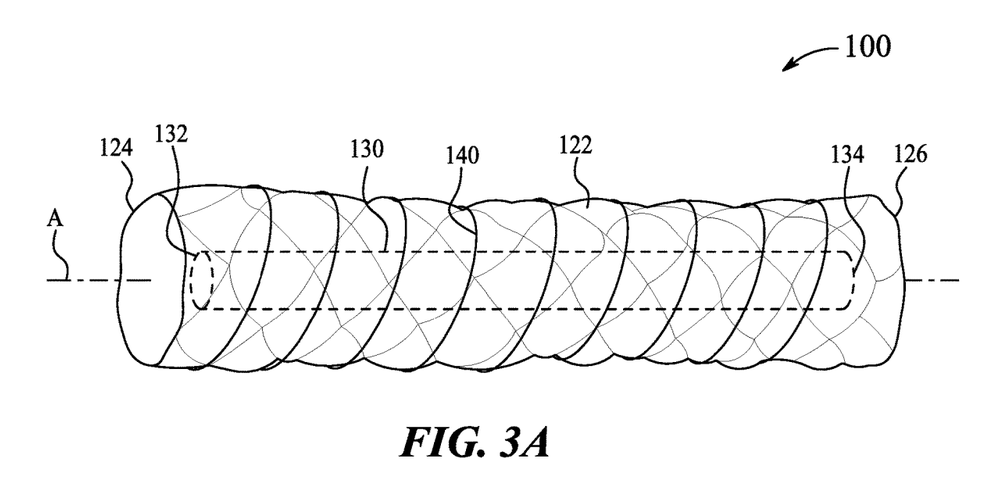
FIG. 3A is a perspective view of the orthodontic absorbing retractor having a braided cotton roll and a flexible hydrophobic plastic thread helically surrounding the braided cotton roll, according to certain embodiments.

Referring to FIG. 3A, a perspective view of the orthodontic absorbing retractor 100 having the flexible hydrophobic plastic thread 140 helically wrapped around the exterior of the braided cotton roll 122 is illustrated. The orthodontic absorbing retractor 100 includes a single strand of the flexible hydrophobic plastic thread 140 helically wrapped around the exterior of the braided cotton roll 122 from the first end 124 to the second end 126 thereof. A distance between two adjacent loops and a cross sectional area of the flexible hydrophobic plastic thread 140 may be defined based on various parameters such as the size of the orthodontic absorbing retractor 100 including the roll length '$L_r$,' and the second diameter '$D_2$' of the braided cotton roll 122, and an amount of cotton filaments used per unit volume of the orthodontic absorbing retractor 100. In an example, the flexible hydrophobic plastic thread 140 may be spun from hydrophobic polymers, such as polyethylene, polypropylene, and vinyl polymers such as polyvinyl chloride.

Figure 3B:
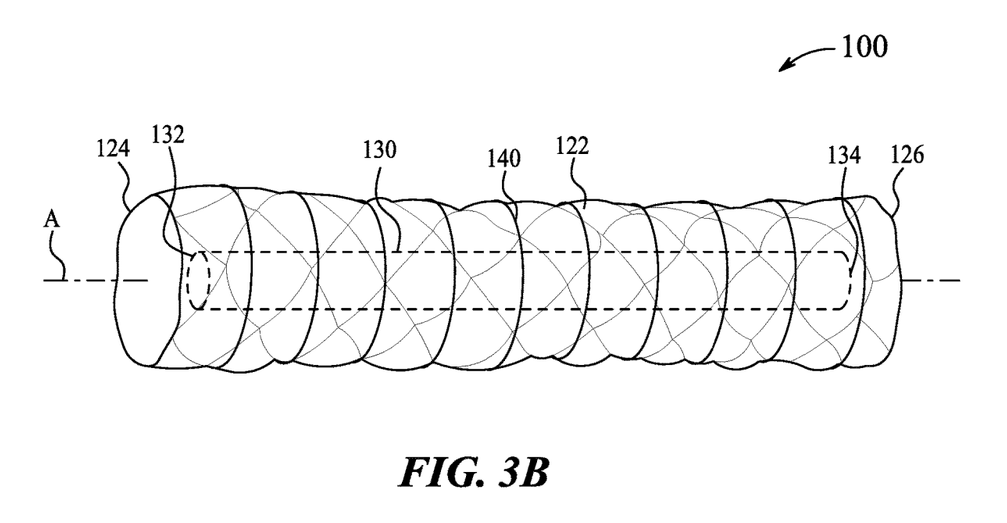
FIG. 3B is a perspective view of the orthodontic absorbing retractor having the flexible hydrophobic plastic thread wrapped around the braided cotton roll perpendicular to a central axis thereof, according to certain embodiments.

Referring to FIG. 3B, a perspective view of the orthodontic absorbing retractor 100 having the flexible hydrophobic plastic thread 140 wrapped around the exterior of the braided cotton roll 122 perpendicular to the central axis 'A' thereof is illustrated. Particularly, a plane defined by a single circular loop of the flexible hydrophobic plastic thread 140 is perpendicular to the central axis 'A' of the braided cotton roll 122. In one example, multiple circular loops of the flexible hydrophobic plastic thread 140 may be wrapped around the braided cotton roll 122. In another example, a single strand of the flexible hydrophobic plastic thread 140 may be wrapped around the braided cotton roll 122 from the first end 124 to the second end 126 such that a plane defined by a single loop may be at an angle in a range of 85 to 95 degrees with respect to the central axis 'A' of the braided cotton roll 122. A distance between two adjacent loops and a cross sectional area of the flexible hydrophobic plastic thread 140 may be defined based on parameters such as the size of the orthodontic absorbing retractor 100 and an amount of cotton filaments used per unit volume of the orthodontic absorbing retractor 100.

Figure 3C:
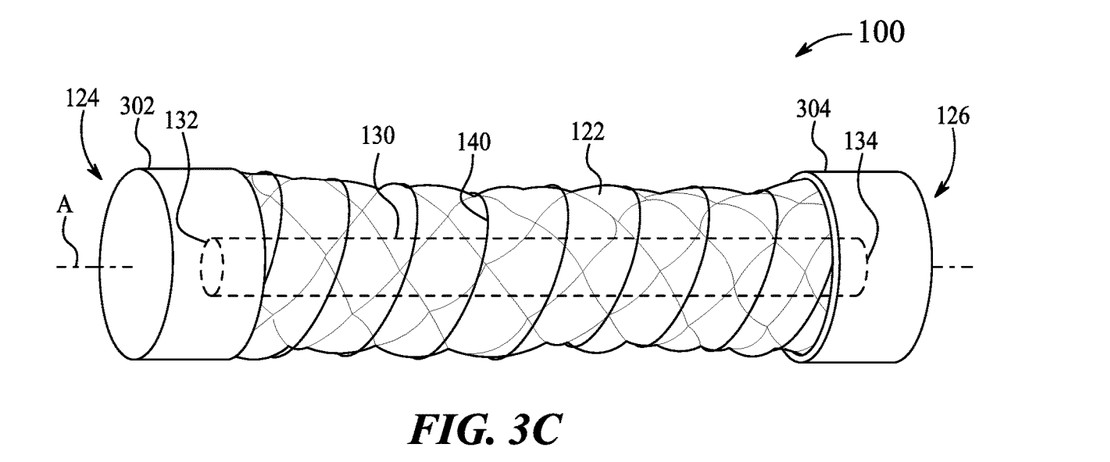
FIG. 3C is a perspective view of the orthodontic absorbing retractor having a first end and a second end with end caps, according to certain embodiments.

Referring to FIG. 3C, a perspective view of the orthodontic absorbing retractor 100 having the first end 124 and the second end 126 covered by a first end cap 302 and a second end cap 304, respectively, is illustrated. The first end cap 302 is configured to sheathe the first wire end 132 of the shape retention wire 130 and the second end cap 304 is configured to sheathe the second wire end 134 of the shape retention wire 130. The first end cap 302 and the second end cap 304 are attached to the first end 124 and the second end 126, respectively, of the braided cotton roll 122. Such arrangement prevents the shape retention wire 130 from sticking out during bending of the orthodontic absorbing retractor 100. In an example, the first end cap 302 and the second end cap 304 may be attached to the braided cotton roll 122 using an adhesive. Further, the first end cap 302 and the second end cap 304 prevent sticking of the first end 124 and the second end 126 of the braided cotton roll 122 during the orthodontic procedure. The first end cap 302 and the second end cap 304 may be made of materials such as biocompatible metal or biocompatible plastic. Further, the first end cap 302 and the second end cap 304 may be made of hydrophobic polymeric material or hydrophilic polymeric material. The first end cap 302 and the second end cap 304 are made of soft and compressible biocompatible material such that the end caps do not abrade the mouth 102 of the patient during the orthodontic procedure.

Figure 3D:
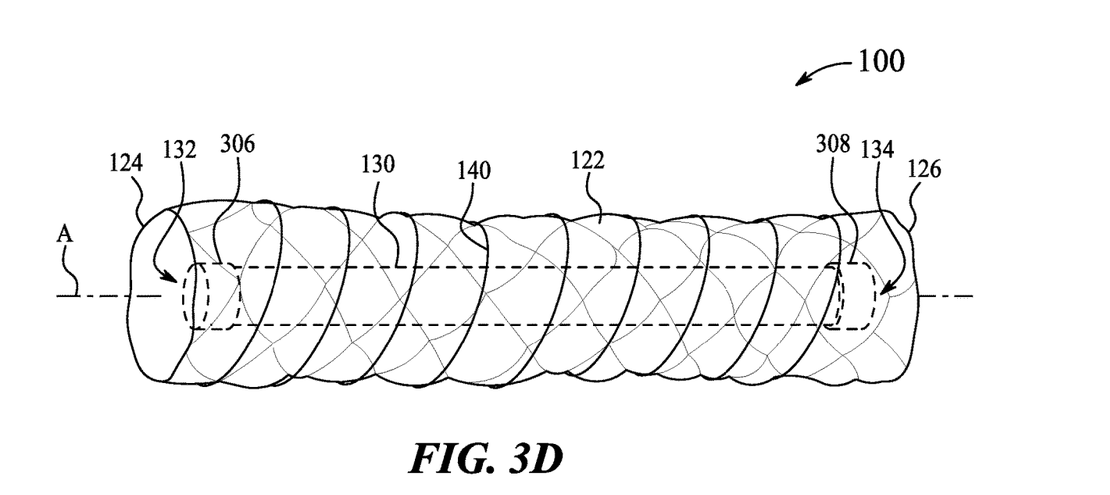
FIG. 3D is a perspective view of the orthodontic absorbing retractor having a shape retention wire with end caps, according to certain embodiments.

Referring to FIG. 3D, a perspective view of the orthodontic absorbing retractor 100 having the first wire end 132 and the second wire end 134 of the shape retention wire 130 covered by a first wire end cap 306 and a second wire end cap 308, respectively, is illustrated. In one example, the first wire end cap 306 and the second wire end cap 308 may be attached with the first wire end 132 and the second wire end 134 of the shape retention wire 130 as integral components during manufacturing thereof. In another example, the first wire end cap 306 and the second wire end cap 308 may be separately attached to the first wire end 132 and the second wire end 134 of the shape retention wire 130. Particularly, each of the first wire end cap 306 and the second wire end cap 308 may have a protrusion extending radially from an inner surface thereof, and the first wire end 132 and the second wire end 134 of the shape retention wire 130 may have a groove or a recess to engage with the protrusion. The first wire end cap 306 and the second wire end cap 308 may be firmly engaged with the first wire end 132 and the second wire end 134, respectively, of the shape retention wire 130. The first wire end cap 306 and the second wire end cap 308 prevent direct contact of the first wire end 132 and the second wire end 134 of the shape retention wire 130 such that injuries to the gum and interior of the mouth 102 may be avoided during the orthodontic procedure.

Although the braided cotton roll 122 is used as the absorbent member in the orthodontic absorbing retractor 100 of the present disclosure, any suitable material that is approved for dental use, capable of absorbing moisture, and used to keep the teeth isolated and dry during the orthodontic procedure may be used as absorbent material such as polymeric fabric having hydrophilicity property. The orthodontic absorbing retractor 100 may include a first visual indicator for different sizes of the orthodontic absorbing retractor 100 such that child and adult sizes can be quickly identified.

Further, the orthodontic absorbing retractor 100 may be provided with a second visual indicator to differentiate the orthodontic absorbing retractor 100 based on the type of material of the shape retention wire 130. In certain example, the orthodontic absorbing retractor 100 may include one visual indicator to differentiate the orthodontic absorbing retractor 100 based on the size thereof and material type of the shape retention wire 130. In one example, the braided cotton roll 122 may be provided with different colors to indicate the size of the orthodontic absorbing retractor 100 and the material type of the shape retention wire 130. In another example, the flexible hydrophobic plastic thread 140 may be provided with different colors to indicate the size of the orthodontic absorbing retractor 100 and the material type of the shape retention wire 130. In some examples, the first visual indicator, the second visual indicator, or both the first and second visual indicators may be printed, embossed, or debossed on the first end cap 302 or the second end cap 304. Further, the braided cotton roll 122 or the flexible hydrophobic plastic thread 140 may be provided with different flavoring agents to make the orthodontic procedure more pleasant and enjoyable to the patient.

Figure 4:
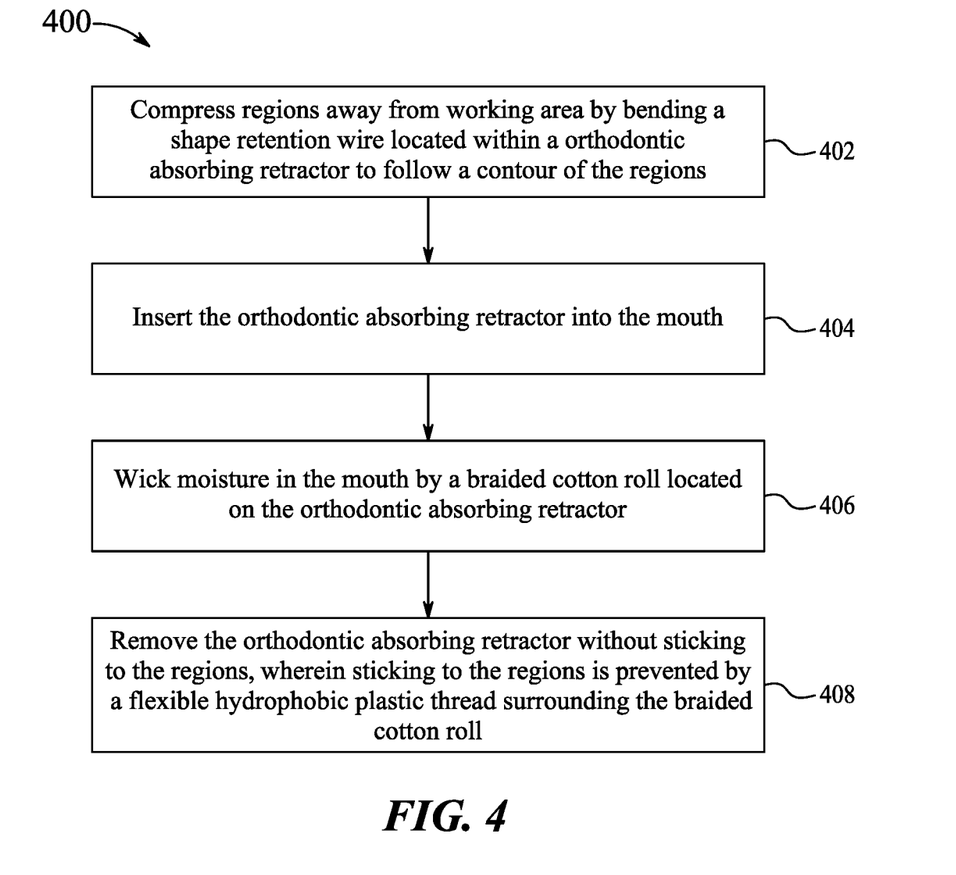
FIG. 4 is an exemplary flowchart of a method for retracting regions of a working area of the mouth with the orthodontic absorbing retractor, according to certain embodiments.

Referring to FIG. 4, an exemplary flowchart of a method 400 for retracting regions of the working area 108 of the mouth 102 with the orthodontic absorbing retractor 100 is illustrated. The method 400 is described with reference to the orthodontic absorbing retractor 100 as illustrated in FIG. 1 through FIG. 3D.

At step 402, the method 400 includes compressing the regions away from the working area 108 by bending the shape retention wire 130 located within the orthodontic absorbing retractor 100 to follow the contour of the regions. The method 400 further includes bending the shape retention wire 130 into the U-shaped bend before inserting the orthodontic absorbing retractor 100 into the mouth 102. During the orthodontic procedure, the dentist diagnoses the working area 108 in the mouth 102 of the patient. In one example, the working area 108 may be the lower front teeth region of the mouth 102. In such a case, the dentist measures the U-shape of the lower teeth structure 104 of the patient. Based on the U-shape of the lower teeth structure 104, the orthodontic absorbing retractor 100 is bent into the U-shape in conformance with the U-shape of the lower teeth structure 104. The shape retention wire 130 located within the orthodontic absorbing retractor 100 is bent to cause the orthodontic absorbing retractor 100 to remain in the U-shape. Particularly, the shape retention wire 130 is bent to follow the contour of the lower front teeth region of the mouth 102. Thus, the orthodontic absorbing retractor 100 along with the shape retention wire 130 is bent corresponding to the shape of the lower front teeth region to compress the regions away therefrom. In another example, the working area 108 may be the upper front teeth region of the mouth 102. In such a case, the dentist measures the U-shape of the upper teeth structure 106 of the patient and bends the orthodontic absorbing retractor 100 along with the shape retention wire 130 to follow the contour of the upper front teeth region of the mouth 102.

The method 400 may further include bending the shape retention wire 130 into a C-shaped bend before inserting the orthodontic absorbing retractor 100 into the mouth 102. In one example, the working area 108 may be the location proximate the parotid papilla gland in the buccal vestibule region 110 of the mouth 102. In such a case, the dentist measures the upper gum region and the lower gum region of the mouth 102 of the patient and bend the orthodontic absorbing retractor 100 along with the shape retention wire 130 into the C-shape to follow the contour of the upper gum region and the lower gum region. In all such cases, the first end 124 and the second end 126 of the orthodontic absorbing retractor 100 are opened wider than the corresponding shape of the working area 108 of the mouth 102 to cause the pressure on the lingual side or the facial side of the teeth structures.

At step 404, the method 400 further include a inserting the orthodontic absorbing retractor 100 into the mouth 102. Particularly, the method 400 may include inserting the orthodontic absorbing retractor 100 such that the U-shaped bend faces towards the front region of the mouth 102 and the first end 124 and the second end 126 face towards the back region of the mouth 102, and pressing the orthodontic absorbing retractor 100 against the contour of the gum region of the mouth 102. In one example, the method 400 includes inserting the orthodontic absorbing retractor 100 such that the U-shaped bend is beneath the tongue region of the mouth 102 and presses against the contour of the gum region beneath the lower front teeth region of the mouth 102. The orthodontic absorbing retractor 100 is placed beneath the lower teeth structure 104 and the tongue region such as the underside of the tongue 112. As the first end 124 and the second end 126 of the orthodontic absorbing retractor 100 are opened wider than the U-shape of the lower front teeth region, the orthodontic absorbing retractor 100 is firmly positioned and pressed against the lingual side of the lower teeth structure 104.

In another example, the method 400 may include inserting the orthodontic absorbing retractor 100 such that the U-shaped bend is above the upper front teeth region of the mouth 102 and presses against the contour of the exterior surface of the gum. Particularly, the orthodontic absorbing retractor 100 is placed between the upper front teeth region, and the upper lip region and the cheek such that the orthodontic absorbing retractor 100 is firmly positioned and pressed against the facial side of the upper teeth structure 106.

In another example, the method 400 may include inserting the orthodontic absorbing retractor 100 such that the C-shaped bend is proximate the parotid papilla gland in the buccal vestibule region 110 of the mouth 102. The first end 124 presses against the upper gum region of the mouth 102 and the second end 126 presses towards the lower gum region of the mouth 102. Further, the orthodontic absorbing retractor 100 is pressed against the side of the mouth 102 to isolate the upper gum region and the lower gum region from the cheek wall of the mouth 102.

At step 406, the method 400 includes wicking moisture in the mouth 102 by the braided cotton roll 122 located on the orthodontic absorbing retractor 100. With the inherent moisture absorbing properties of the cotton filaments of the braided cotton roll 122, orthodontic absorbing retractor 100 absorbs the moisture coming from saliva, gum fluids, blood and water. As such, the moisture from the working area 108 is wicked by the orthodontic absorbing retractor 100 while isolating and retracting the regions away from the working area 108 of the mouth 102.

At step 408, the method 400 includes removing the orthodontic absorbing retractor 100 without sticking to the regions, wherein sticking to the regions is prevented by the flexible hydrophobic plastic thread 140 surrounding the braided cotton roll 122. Upon complete soaking of the braided cotton roll 122, the orthodontic absorbing retractor 100 is removed from the working area 108 of the mouth 102. As the braided cotton roll 122 is surrounded by the flexible hydrophobic plastic thread 140, the braided cotton roll 122 does not stick to the interior surface of the working area 108 of the mouth 102 and the orthodontic absorbing retractor 100 easily comes out of the working area 108.

Figure 5:
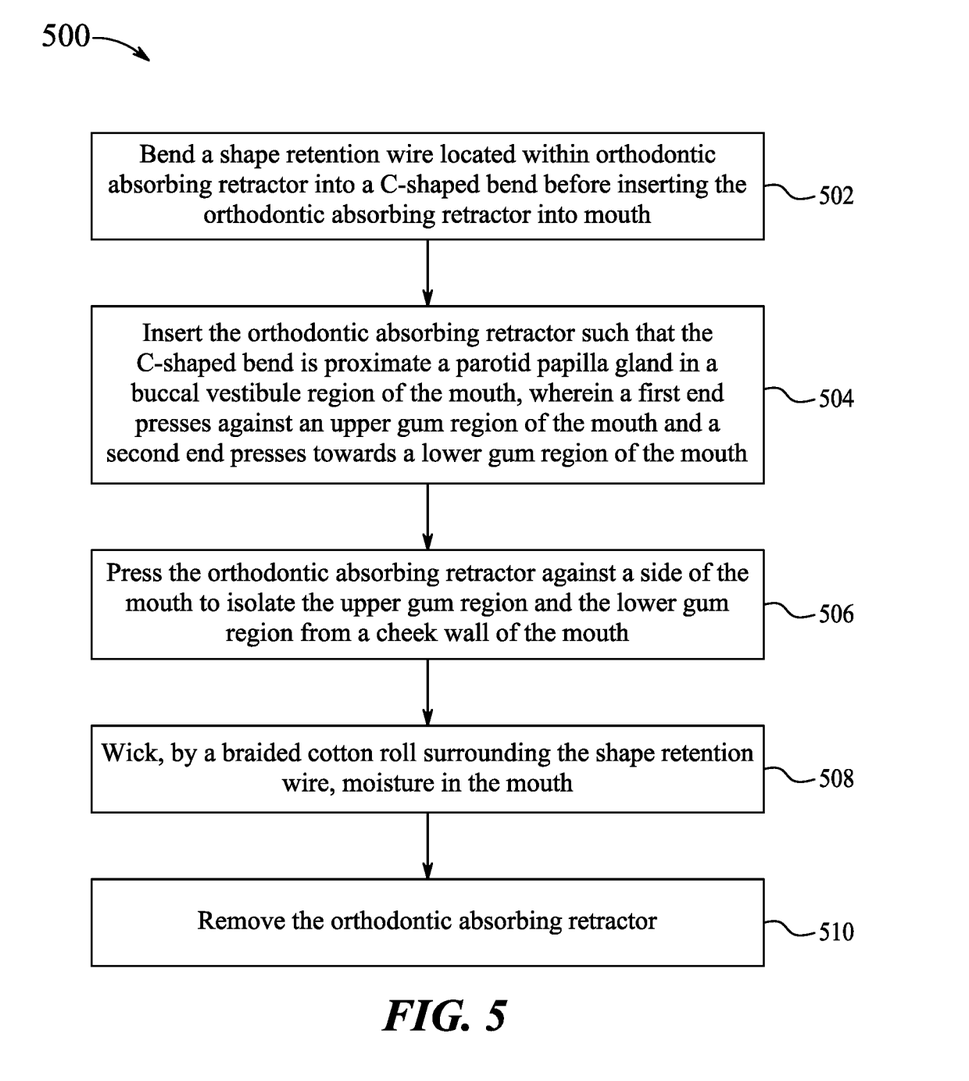
FIG. 5 is an exemplary flowchart of a method for retracting buccal vestibule regions of the mouth with the orthodontic absorbing retractor, according to certain embodiments.

Referring to FIG. 5, an exemplary flowchart of a method 500 for retracting regions of the mouth 102 with the orthodontic absorbing retractor 100 is illustrated. The method 500 is described with reference to the orthodontic absorbing retractor 100 bent as illustrated in FIG. 1 through FIG. 3D.

At step 502, the method 500 includes bending the shape retention wire 130 located within the orthodontic absorbing retractor 100 into a C-shaped bend before inserting the orthodontic absorbing retractor 100 into the mouth 102. The orthodontic absorbing retractor 100 is bent into the C-shaped bend based on the shape of the working area 108 of the mouth 102 before inserting the orthodontic absorbing retractor 100 into the mouth 102. The shape retention wire 130 located within the orthodontic absorbing retractor 100 is bent to cause the orthodontic absorbing retractor 100 to remain in the C-shape. Particularly, the shape retention wire 130 is bent to follow the contour of the buccal vestibule region 110 of the mouth 102.

At step 504, the method 500 includes inserting the orthodontic absorbing retractor 100 such that the C-shaped bend is proximate the parotid papilla gland in the buccal vestibule region 110 of the mouth 102. In the case of buccal vestibule region 110 of the mouth 102, the orthodontic absorbing retractor 100 is inserted in such a way that the C-shaped bend is placed proximate the parotid papilla gland, and the first end 124 is pressed against the upper gum region of the mouth 102 and the second end 126 is pressed towards the lower gum region of the mouth 102.

At step 506, the method 500 includes pressing the orthodontic absorbing retractor 100 against the side of the mouth 102 to isolate the upper gum region and the lower gum region from the cheek wall of the mouth 102.

At step 508, the method 500 includes wicking, by the braided cotton roll 122 surrounding the shape retention wire 130, moisture in the mouth 102. The braided cotton roll 122 of the orthodontic absorbing retractor 100 absorbs the moisture coming from saliva, gum fluids, blood and water, while isolating and retracting the regions away from the working area 108 of the mouth 102.

At step 510, the method 500 includes removing the orthodontic absorbing retractor 100. As the braided cotton roll 122 is surrounded by the flexible hydrophobic plastic thread 140, the braided cotton roll 122 is prevented from sticking to the regions of the working area 108 of the mouth 102.

The first embodiment of the present disclosure is illustrated with respect to FIG. 1 through FIG. 3D. The first embodiment describes the orthodontic absorbing retractor 100 for use in the mouth 102 of the patient. The orthodontic absorbing retractor 100 comprises the braided cotton roll 122 having the cylindrical shape, wherein the braided cotton roll 122 has the central axis 'A', the first end 124 and the second end 126; the shape retention wire 130 coaxially located within the braided cotton roll 122 between the first end 124 and the second end 126; and the flexible hydrophobic plastic thread 140 wrapped around the exterior of the braided cotton roll 122 from the first end 124 to the second end 126. The flexible hydrophobic plastic thread 140 is configured to prevent sticking of the orthodontic absorbing retractor 100 to the interior surface of the mouth 102.

In the orthodontic absorbing retractor 100, the shape retention wire 130 is copper.

In the orthodontic absorbing retractor 100, the shape retention wire 130 is aluminum.

In the orthodontic absorbing retractor 100, the shape retention wire 130 is 0.03 inches in diameter and has a wire length '$L_w$' in the range of 3.0 to 5.6 inches long; and the braided cotton roll 122 is 0.375 inches in diameter and has a roll length '$L_r$' in the range of 3.4 to 6.0 inches long.

In the orthodontic absorbing retractor 100, the shape retention wire 130 has the first diameter, $D_1$, and the wire length, $L_w$; the braided cotton roll 122 has the second diameter, $D_2$, and the roll length, $L_r$; wherein $D_1<D_2$, $D_1$ is in the range of 0.025 inches to 0.035 inches and $D_2$ is in the range of 0.3 to 0.4 inches; and wherein $L_w<L_r$, $L_w$ is in the range of 3.0 to 5.6 inches long and $L_r$ is in the range of 3.4 to 6.0 inches long.

In the orthodontic absorbing retractor 100, the braided cotton roll 122 includes cotton filaments.

In the orthodontic absorbing retractor 100, the flexible hydrophobic plastic thread 140 is wrapped around the exterior of the braided cotton roll 122 such that the flexible hydrophobic plastic thread 140 is perpendicular to the central axis 'A'.

In the orthodontic absorbing retractor 100, the flexible hydrophobic plastic thread 140 is helically wrapped around the exterior of the braided cotton roll 122.

The orthodontic absorbing retractor 100 further comprises the first end cap 302 configured to sheathe the first wire end 132 of the shape retention wire 130; and the second end cap 304 configured to sheathe the second wire end 134 of the shape retention wire 130.

The orthodontic absorbing retractor 100 further comprises the first wire end 132 of the shape retention wire 130 having the rounded shape; and the second wire end 134 of the shape retention wire 130 having the rounded shape.

In the orthodontic absorbing retractor 100, the flexible hydrophobic plastic thread 140 is a biocompatible hydrophobic material.

In the orthodontic absorbing retractor 100, the biocompatible hydrophobic material is medical grade nylon.

In the orthodontic absorbing retractor 100, the biocompatible hydrophobic material is polytetrafluoroethylene.

The second embodiment of the present disclosure is illustrated with respect to FIG. 1 through FIG. 4. The second embodiment describes the method 400 for retracting regions of the working area 108 of the mouth 102 with the orthodontic absorbing retractor 100. The method 400 comprises compressing the regions away from the working area 108 by bending the shape retention wire 130 located within the orthodontic absorbing retractor 100 to follow the contour of the regions; inserting the orthodontic absorbing retractor 100 into the mouth 102; wicking moisture in the mouth 102 by the braided cotton roll 122 located on the orthodontic absorbing retractor 100; and removing the orthodontic absorbing retractor 100 without sticking to the regions, wherein sticking to the regions is prevented by the flexible hydrophobic plastic thread 140 surrounding the braided cotton roll 122.

The method 400 further comprises bending the shape retention wire 130 into the U-shaped bend before inserting the orthodontic absorbing retractor 100 into the mouth 102; inserting the orthodontic absorbing retractor 100 such that the U-shaped bend is towards the front region of the mouth 102 and the first end 124 and the second end 126 are towards the back region of the mouth 102; and pressing the orthodontic absorbing retractor 100 against the contour of the gum region of the mouth 102.

The method 400 further comprises inserting the orthodontic absorbing retractor 100 such that the U-shaped bend is beneath the tongue region of the mouth 102 and presses against the contour of the gum region beneath the lower front teeth region of the mouth 102.

The method 400 further comprises inserting the orthodontic absorbing retractor 100 such that the U-shaped bend is above the tongue region of the mouth 102 and presses against the contour of the gum region above the upper front teeth region of the mouth 102.

The method 400 further comprises bending the shape retention wire 130 into the C-shaped bend before inserting the orthodontic absorbing retractor 100 into the mouth 102; inserting the orthodontic absorbing retractor 100 such that the C-shaped bend is proximate the parotid papilla gland in the buccal vestibule region 110 of the mouth 102, wherein the first end 124 presses against the upper gum region of the mouth 102 and the second end 126 presses towards the lower gum region of the mouth 102; and pressing the orthodontic absorbing retractor 100 against the side of the mouth 102 to isolate the upper gum region and the lower gum region from the cheek wall of the mouth 102.

The third embodiment of the present disclosure is illustrated with respect to FIG. 1 through FIG. 3D, and FIG. 5. The third embodiment describes the method 500 for retracting the regions of the mouth 102 with the orthodontic absorbing retractor 100. The method 500 comprises bending the shape retention wire 130 located within the orthodontic absorbing retractor 100 into a C-shaped bend before inserting the orthodontic absorbing retractor 100 into the mouth 102; inserting the orthodontic absorbing retractor 100 such that the C-shaped bend is proximate the parotid papilla gland in the buccal vestibule region 110 of the mouth 102, in which the first end 124 presses against the upper gum region of the mouth 102 and the second end 126 presses towards the lower gum region of the mouth 102; pressing the orthodontic absorbing retractor 100 against the side of the mouth 102 to isolate the upper gum region and the lower gum region from the cheek wall of the mouth 102; wicking the moisture in the mouth 102 by the braided cotton roll 122 surrounding the shape retention wire 130; and removing the orthodontic absorbing retractor 100.

In the method 500, sticking to the mouth regions is prevented by the flexible hydrophobic plastic thread 140 surrounding the braided cotton roll 122.

Obviously, numerous modifications and variations of the present disclosure are possible in light of the above teachings. It is therefore to be understood that within the scope of the appended claims, the invention may be practiced otherwise than as specifically described herein.

The invention claimed is:

1. An orthodontic absorbing retractor for use in a mouth of a patient, comprising:
 a braided cotton roll having a cylindrical shape, wherein the braided cotton roll has a central axis, a first end and a second end;
 a shape retention wire coaxially located within the braided cotton roll between the first end and the second end; and
 a flexible hydrophobic plastic thread wrapped around an exterior of the braided cotton roll from the first end to the second end, the flexible hydrophobic plastic thread configured to prevent sticking of the orthodontic absorbing retractor to an interior surface of the mouth.

2. The orthodontic absorbing retractor of claim 1, wherein the shape retention wire is copper.

3. The orthodontic absorbing retractor of claim 1, wherein the shape retention wire is aluminum.

4. The orthodontic absorbing retractor of claim 1, wherein:
 the shape retention wire is 0.03 inches in diameter and has a wire length in a range of 3.0 to 5.6 inches long; and
 the braided cotton roll is 0.375 inches in diameter and has a roll length in a range of 3.4 to 6.0 inches long.

5. The orthodontic absorbing retractor of claim 1, wherein:
 the shape retention wire has a first diameter, $D_1$, and a wire length, $L_w$;
 the braided cotton roll has a second diameter, $D_2$, and a roll length, $L_r$;
 wherein $D_1 < D_2$, $D_1$ is in a range of 0.025 inches to 0.035 inches and $D_2$ is in a range of 0.3 to 0.4 inches; and
 wherein $L_w < L_r$, $L_w$ is in a range of 3.0 to 5.6 inches long and $L_r$ is in a range of 3.4 to 6.0 inches long.

6. The orthodontic absorbing retractor of claim 1, wherein the braided cotton roll includes cotton filaments.

7. The orthodontic absorbing retractor of claim 1, wherein the flexible hydrophobic plastic thread is wrapped around the exterior of the braided cotton roll such that the flexible hydrophobic plastic thread is perpendicular to the central axis.

8. The orthodontic absorbing retractor of claim 1, wherein the flexible hydrophobic plastic thread is helically wrapped around the exterior of the braided cotton roll.

9. The orthodontic absorbing retractor of claim 1, further comprising:
 a first end cap configured to sheathe a first wire end of the shape retention wire; and
 a second end cap configured to sheathe a second wire end of the shape retention wire.

10. The orthodontic absorbing retractor of claim 1, further comprising:
 a first wire end of the shape retention wire having a rounded shape; and
 a second wire end of the shape retention wire having a rounded shape.

11. The orthodontic absorbing retractor of claim 1, wherein the flexible hydrophobic plastic thread is a biocompatible hydrophobic material.

12. The orthodontic absorbing retractor of claim 11, wherein the biocompatible hydrophobic material is medical grade nylon.

13. The orthodontic absorbing retractor of claim 11, wherein the biocompatible hydrophobic material is polytetrafluoroethylene.

* * * * *